United States Patent [19]
Kroll et al.

[11] Patent Number: 5,265,623
[45] Date of Patent: Nov. 30, 1993

[54] OPTIMIZED FIELD DEFIBRILLATION CATHETER

[75] Inventors: Mark W. Kroll, Minnetonka; Byron L. Gilman, Plymouth, both of Minn.

[73] Assignee: Angeion Corporation, Plymouth, Minn.

[21] Appl. No.: 915,063

[22] Filed: Jul. 16, 1992

[51] Int. Cl.⁵ .............................................. A61N 1/05
[52] U.S. Cl. ................................. 607/122; 128/419 D
[58] Field of Search ................... 128/419 D, 642, 784, 128/785, 786, 639

[56] References Cited

U.S. PATENT DOCUMENTS

| | | | |
|---|---|---|---|
| 3,769,984 | 11/1973 | Muench | 128/786 |
| 4,603,705 | 8/1986 | Speicher et al. | 128/786 |
| 4,630,611 | 12/1986 | King | 128/786 |
| 5,044,375 | 9/1991 | Bach, Jr. et al. | 128/786 |

*Primary Examiner*—William E. Kamm
*Assistant Examiner*—George Manuel
*Attorney, Agent, or Firm*—Joel D. Skinner

[57] ABSTRACT

A defibrillation catheter having a connection from an electrode to an infeed conductor in the mid-point area of the electrode. The mid-point current feed provides for a voltage drop from the center of the electrode to its ends, which minimizes extreme electrical fields which normally develop at the electrode ends. The coil resistance is selected to further optimize the field distribution so as to allow a large passage of defibrillation current without cell damage.

16 Claims, 4 Drawing Sheets

OPTIMIZED FIELD DEFIBRILLATION CATHETER

BACKGROUND OF THE INVENTION

This invention relates to electromedical apparatus and particularly to medical electrode catheter apparatus. The device is particularly useful as a transvenous electrode catheter for use as part of an implantable cardiac defibrillation system.

In the past, various catheter or lead electrode devices have been used and proposed for use in conjunction with implantable cardiac defibrillator devices to automatically provide a current pulse to the heart upon the occurrence of a predetermined cardiac event, such as tachycardia for example. However, the prior art devices are generally complex, difficult to construct and utilize, and are inefficient to use. A particular problem present in prior art devices is the phenomenon of uneven current distribution around the electrodes of the catheters or leads.

The first defibrillation catheter with coil-type electrode of which the inventors are aware is disclosed in U.S. Pat. No. 3,614,955 (Mirowski) and U.S. Pat. No. 3,942,536 (Mirowski). U.S. Pat. No. 4,355,646 (Kallok) shows solid rings for electrode "coils". U.S. Pat. No. 4,499,907 (Kallok) depicts a defibrillator catheter with an integral resistor to limit current to the entire electrode coil. It does not, however, affect the current distribution at the ends vs. the center of the electrode. U.S. Pat. No. 4,603,705 (Speicher et al.) discloses a defibrillator catheter combining pacing functions. U.S. Pat. Nos. 4,860,769 and 4,865,037 (Fogarty) show a coiled ribbon and a coiled catheter tip. U.S. Pat. No. 4,932,407 (Williams) discloses a ribbon coil. These prior art defibrillation catheters have lead connections at one or both ends of their respective electrodes. U.S. Pat. No. 4,969,463 (Dahl) shows a catheter which allows control of the energy delivered to different parts of the coil. The coil is broken up into several rings and each has its own conductor. Thus, each section can receive a different pulse. However, such a design would be impractical to use with the multiple conductors required.

Despite the need for a cardiac defibrillation catheter in the art which provides optimized field distribution, and which overcomes the limitations and problems of the prior art, none insofar as is known has been proposed or developed. Accordingly, it is an object of the present invention to provide a cardiac defibrillation catheter which yields optimized field distribution, and which is easy to construct and utilize.

SUMMARY OF THE INVENTION

Defibrillating the human heart is accomplished by applying an electrical waveform to the cardiac muscle with appropriate electrodes, causing the cessation of the rapid uncoordinated contractions of the heart (fibrillation), and a restoration of normal beating of the heart.

The present invention a implantable cardiac defibrillation catheter apparatus, comprising at least two conductive electrodes each having a cylindrical configuration. The electrodes further comprise a coiled, elongated, continuous metallic band. The electrodes each have a predetermined axial length of between 4 and 12 cm. The metallic band further has predetermined linear and crossectional dimensions, and a predetermined electrical resistance which is a function of the metallic band crossectional dimension. An elongated, flexible conductive lead is connected to each electrode. Each said lead has first and second ends, the lead first end being connected to its respective electrode at a mid-point location along the axial length therefore, each conductive lead further is electrically insulated from the other lead. The apparatus further has means to connect the lead second end to a current source.

These and other benefits of this invention will become clear from the following description by reference to the drawings.

DESCRIPTION OF THE PREFERRED EMBODIMENT

Figure 1:
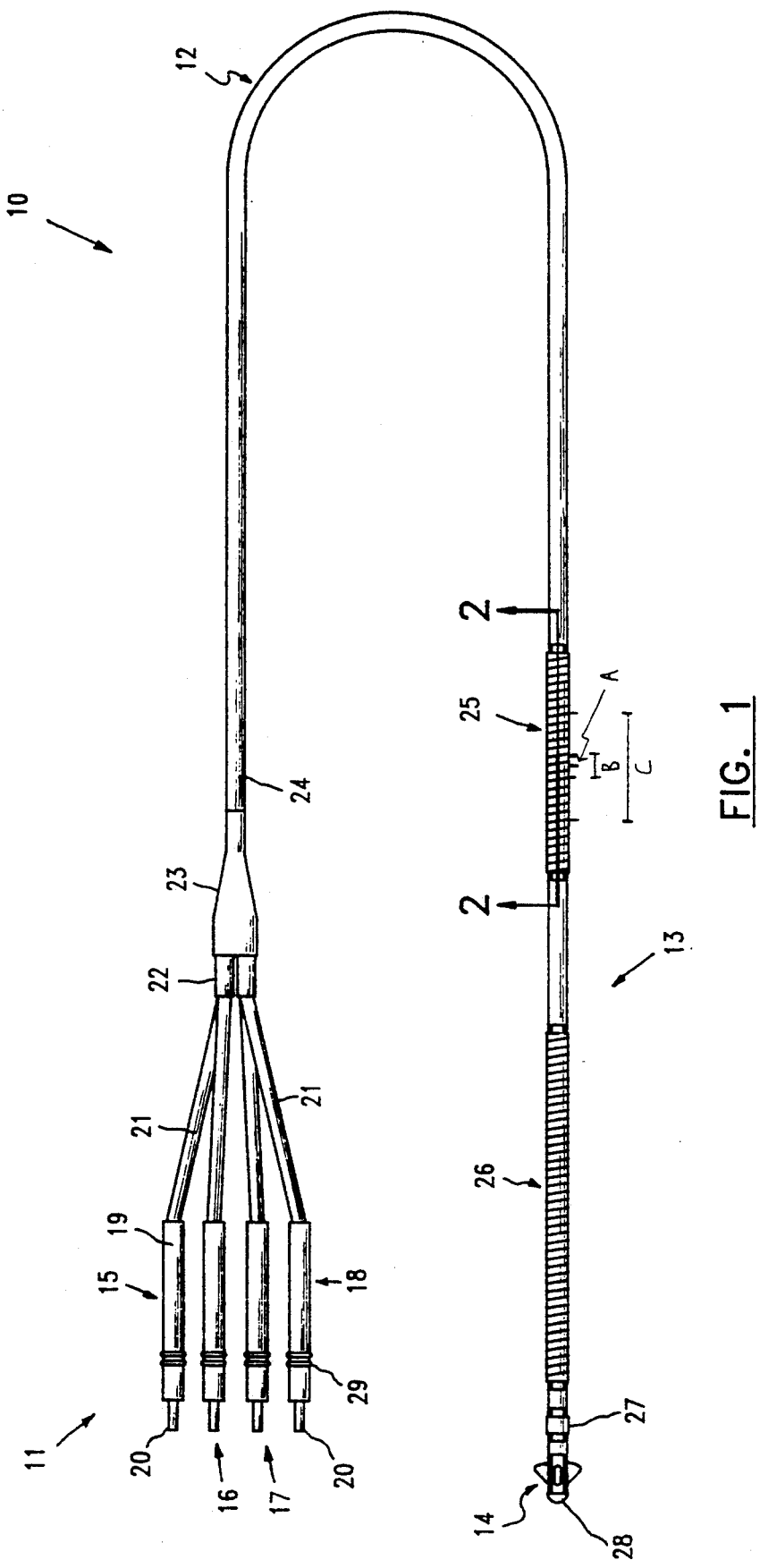
FIG. 1 is a plan view of the optimized field defibrillation catheter of the present invention.

The use of the implantable cardioverter-defibrillator (ICD) is growing rapidly in patients known to be at risk for sudden cardiac death, a syndrome which claims an estimated 400,000 lives per year in the United States. The ICD has further gained in acceptance since recent studies have shown that many anti-arrhythmic drugs have a negative impact on patient survival.

The implantable defibrillator is linked to electrodes which conduct current from the device to the human heart. These electrodes have typically been two or more patches stitched or otherwise secured to the heart. They are referred to as epicardial patch electrodes. Alternatively, to avoid the surgery required for the epicardial patches, large surface area electrode coils are sometimes threaded into the heart chambers through the patient's veins. These are known as transvenous electrodes. One coil-type electrode is typically disposed just above the heart in the right atrium (RA) location and the other is disposed in the right ventricular apex (RVA). Unfortunately, transvenous electrodes are often unable to direct sufficient current through enough of the heart muscle. For this reason, a small patch is additionally inserted just under the skin, on the patient's lower left side. This requires additional, but minimal surgery. This subcutaneous patch is not in direct contact with the heart but allows a current vector starting at a transvenous electrode and going through heart muscle. Thus, the subcutaneous patch assists in directing current thru the heart muscle and hence in defibrillating the heart.

The functional conductive part of the transvenous defibrillation catheter electrode is either a ribbon or coil of wire wrapped around a flexible polymer. This is usually referred to as the "defibrillation coil" regardless of construction. A typical coil diameter is 2-3 mm., and typical lengths of the coil electrode are 4 to 12 cm. The typical catheter lead conductor enters from the left and is attached to the electrode coil at both ends. This provides for a low resistance connection between the lead conductor and the electrode coil. Unfortunately, in this configuration the current distribution around the electrode coil is very uneven. A ring shaped area in the middle of the coil feeds current to a disk-shaped volume of blood. However, each end point of the coil must feed current to a larger hemispherical area of blood. This results in much more current flowing from the ends than from the middle of the coil. Generally, the "sharper" the surface (smaller radii) of the conductor the greater the electrical field that is generated.

This uneven distribution of current causes several problems. First, the extremely high current densities at the coil ends can lead to extremely high fields (volts per cm.) which can damage cells of the blood or heart muscle. Second, decreased defibrillation efficiencies result, due simply to nonhomogeneous currents. Third, high current densities can lead to current limiting when the local blood volume runs out of enough ions to carry the current. These currents can also generate gases through electrolysis, and the gases limit current via their insulating properties. These problems limit the charge transfer to the heart thus decreasing defibrillation effectiveness.

Figure 7:
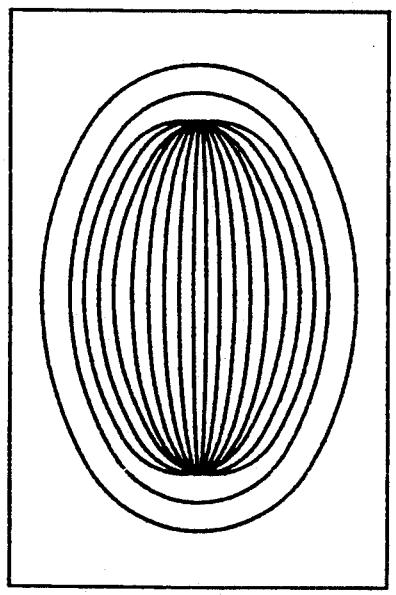
FIG. 7 is a two-dimensional simulation of the voltage distribution around the electrode of a prior art defibrillation catheter; and FIG. is a two dimensional simulation of the voltage distribution around the electrode of the optimized field defibrillation catheter of the present invention.

FIG. 7 shows a two-dimensional simulation of the voltage distribution around a typical prior art defibrillation catheter electrode wherein the current conduction lead is connected at both ends of the catheter electrode. The crowding of the field lines around the electrode ends should be noted. These lines are isopotential lines and each line represents a 20 volt increase over its outer neighbor. The distribution shown is for qualitative purposes only, as the field concentrations will be different in three dimensions.

Referring to FIG. 1, the defibrillation catheter 10 of the present invention is a thin, elongated tubular structure having a connection end 11 for mating with an implantable cardiac defibrillator apparatus (not shown), a cable 12 extending a predetermined length from the connection end 11, and an electrode end 13 disposed at the other end of the cable 12. The electrode end 13 has a predetermined length and terminates in an anchor structure 14 which lodges in cardiac tissue on the interior of the patient's heart.

The connection end 11 is communicatively connectable to the ICD and is shown to have four (4) terminal leads, 15, 16, 17 and 18. Each terminal lead 15–18 comprises a lead plug end 19 having plug end tip 20, an insulated lead conductor 21, and a strain relief sheath 22. All of the terminal leads 15–18 run into a lead collector 23 which interfaces the catheter cable 12.

The electrode end 13 is shown to have four (4) electrodes 25, 26, 27 and 28, spaced at predetermined intervals and corresponding to the leads 15–18. In a typical device 10 application, electrode 25 is a proximal defibrillation electrode, electrode 26 is a distal defibrillation electrode, electrode 27 is a proximal pace/sense electrode, and electrode 28 is a distal pace/sense electrode. As is known in the art, the function of electrodes 25–28 may be varied, depending upon the particular ICD apparatus utilized and the medical application specified, by altering the connection scheme of leads 15–18. When required, one or more of the electrodes 25–28 may be rendered inoperative. Finally, the catheter 10 can be reconfigured, consistent with the teachings of this invention, to have two (2) or three (3) electrodes to suit particular medical applications.

The spacing of the defibrillation electrodes 25 and 26 is a function of the structure and dimensions of the human heart and the prescribed location of the electrodes 25 and 26 therein, typically at the connection of the superior vena cava to the heart and at the left ventricle. Additionally, the length and outer surface area of the electrodes 25 and 26 is selected to maximize current distribution to the patient's heart tissue.

Figure 2:
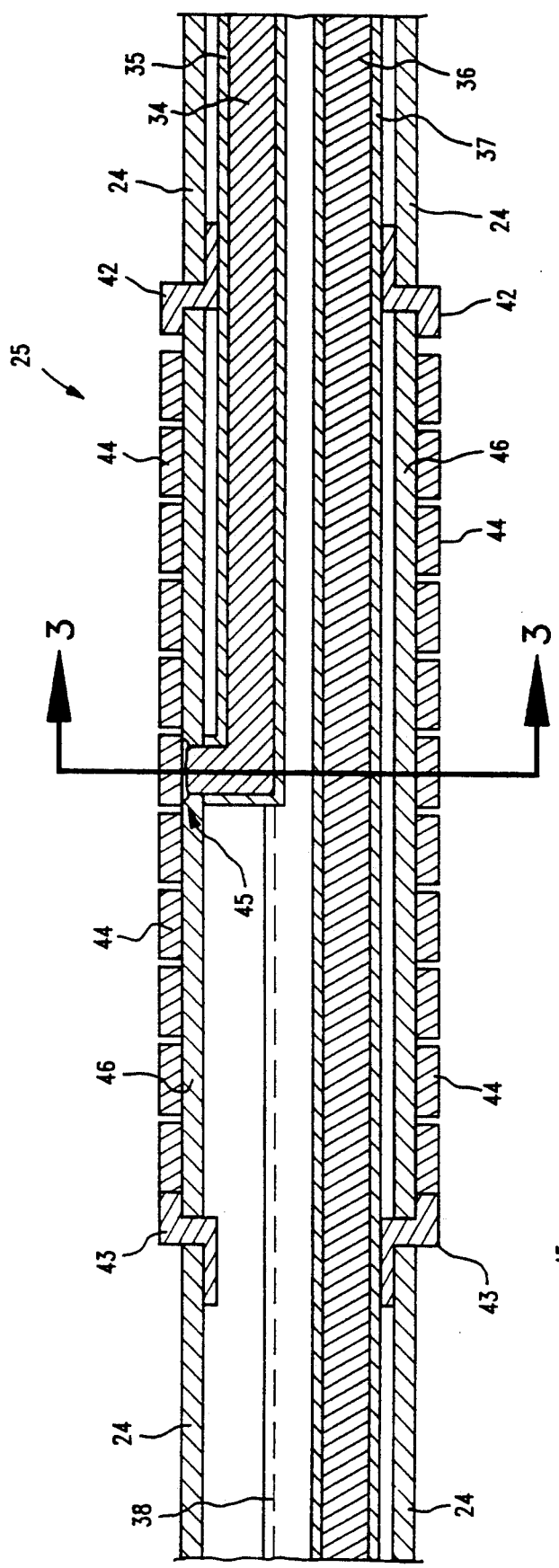
FIG. 2 is a crossectional view of the catheter of FIG. 1, taken along line 2—2 thereof.
Figure 3:
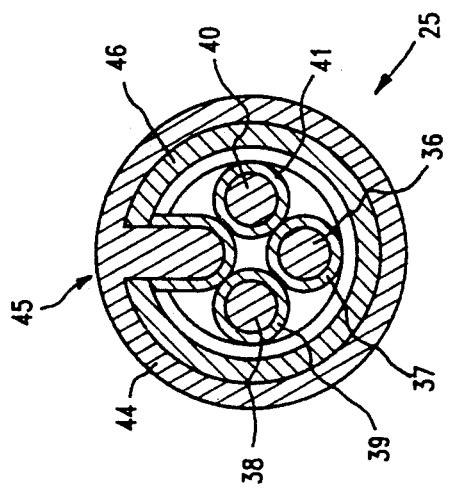
FIG. 3 is a crossectional view of the catheter of FIG. 2, taken along line 3—3 thereof.

Referring also to FIGS. 2 and 3, the cable 12 communicatively connects the leads 15–18 of the connection end 11 with the electrodes 25–28 of the electrode end 13. The multi-lumen cable 12 is shown to comprise four (4) lead conductors 34, 36, 38 and 40. Each lead conductor 34, 36, 38 and 40 has an inner insulator 35, 37, 39 and 41, respectively. Additionally, an outer insulator 24 surrounds the entire group of leads. The leads 34, 36, 38 and 40 are shown to be constructed of a solid conductive, metallic wire. However, they may be constructed of a plurality of twisted strands of wire or a single coiled wire, as is known in the art. The insulators 24, 35, 37, 39 and 41 are preferably constructed of a non-conductive polymeric substance, such as polyurethane, as is known in the art.

The cylindrically configured defibrillation electrodes 2 and 26 preferably comprise a continuous strand of a conductive metallic material 44 which is coiled between a pair of electrode end rings 42 and 43 and wrapped around a base structure. Electrodes having a solid or other configuration may also be utilized to practice the teachings of this invention. Preferred electrode conductive materials include stainless steel, titanium, platinum and various alloys thereof. The over all axial length of the electrodes 25 and 26 are preferably between 4–6 cm. The diameter of the cylindrical electrodes 15 and 16 are preferably between 2–3 mm. Additionally, the electrode coil 44 has a predetermined crossectional width and thickness. Each coil segment is separated from adjacent coil segments a predetermined distance via the above described wrapping.

As shown in FIGS. 2 and 3, lead conductor 34 is connected to the conductive coil 44 of electrode 25, preferably at the mid-point of the axial length of the cylindrical electrode 25. The connection interface 45 of the coil 44 and lead 34 is shown to be made via a weld, although other connection methods and means such as a mechanical connection or connection interface structure may also be used. Defibrillation electrode 26 is connected to lead 36, also at the mid-point of its length.

Supplying current from the lead 34 at the central region of the electrode 25 provides a controlled field distribution around the catheter electrode 25, which in turn provides improved current flow from the catheter 10 to the surrounding blood and heart tissue for defibrillation purposes. Referring to FIG. 1, the mid-point connection (A) is the most preferred point of connection between the lead and the electrode 25 because it is equidistant from each electrode end. However, preferred and acceptable regions of connection on the electrode 25 are shown in the middle 10 percent (B) and 50 percent (C) sections, respectively, of the axial length of the electrode. The spacing from the lead connection point 45 to the electrode ends 42 and 43 allows for a voltage drop from the center of the electrode 25 to the ends, which minimizes extreme fields which may otherwise develop at the ends.

Additionally, the coil 44 material and coil crossectional dimensions are preferably selected to yield a predetermined internal resistance for the coil 44, and to thus further control the field distribution around the electrode 25. An optimum resistance of approximately 10 ohms from the middle of the electrode 25 to an end results in improved field distribution so as to allow passage of a large defibrillation current without cardiac tissue damage which would otherwise occur.

Figure 8:
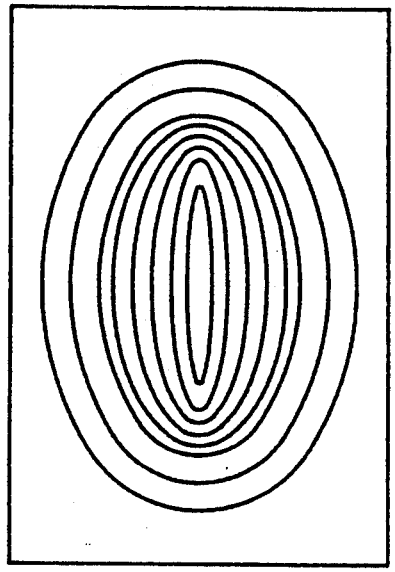

FIG. 8 is a two-dimensional simulation of the expected voltage distribution around a defibrillation catheter 10 electrode 25 in accordance with the present invention. Each isopotential line represents a 20 volt increase over its outer neighbor. Current is fed to the defibrillation electrode 25 at the center of the coil 44 as shown in FIG. 2, for example. The coil 44 resistance allows the voltage along the electrode 25 to taper off as it approaches the ends 42 and 43. In this simulation, the voltage is allowed to decay to 50 percent of the center voltage by the time it reaches the electrode 25 ends.

Figure 4:
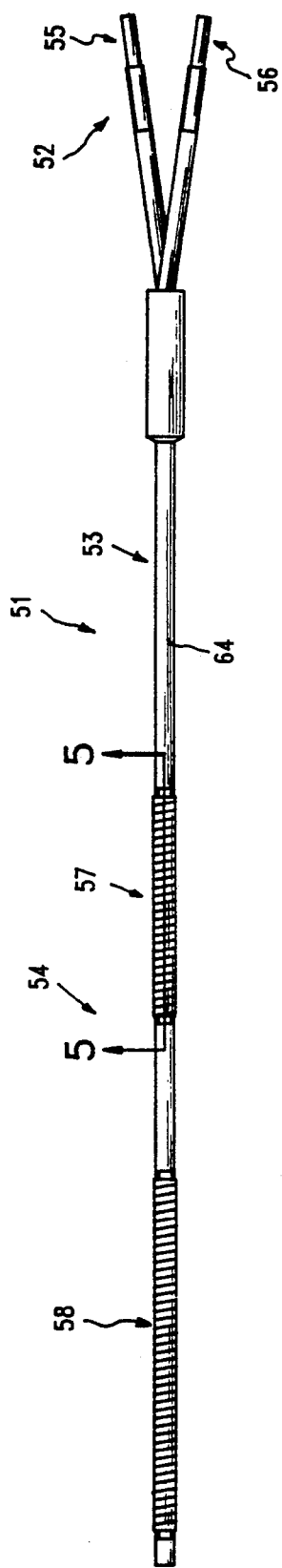
FIG. 4 is a plan view of another embodiment of the optimized field defibrillation catheter of this invention.
Figure 5:
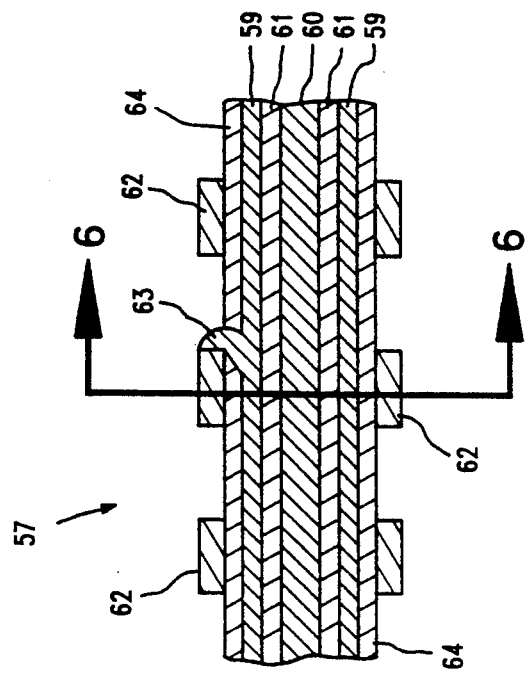
FIG. 5 is a crossectional view of the catheter of FIG. 4, taken along line 5—5 thereof.

Referring to FIGS. 4 and 5, an alternative embodiment of the defibrillation catheter 51 of this invention is shown. The catheter 51 basically comprises an ICD connection end 52, an insulated cable 53 and an electrode end 54. A pair of leads 55 and 56 extend from the connection end 52, through the cable 53 to a pair of cylindrically configured electrodes 57 and 58 disposed at the electrode end 54. As previously discussed with respect to the multi-lumen catheter 10 embodiment, the overall exterior dimensions of this particular catheter 51 embodiment are dependent upon several factors which are known. And although only two (2) electrodes 57 and 58 are shown, the catheter 51 can be reconfigured, consistent with the teachings of this invention, with three (3) or more electrodes to meet specific medical applications.

Figure 6:
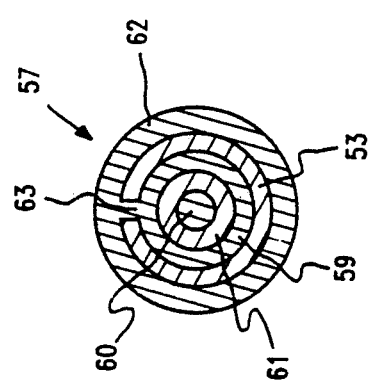
FIG. 6 is a crossectional view of the catheter of FIG. 5, taken along line 6—6 thereof.

Referring to FIGS. 5 and 6, the coaxial cable 53 is shown comprising an outer insulator 64, a first conductive lead 59, an inner insulator 61, and a second conductive lead 60. These elements are all arranged in a layered, coaxial configuration.

Also as shown in FIGS. 5 and 6, the electrodes 57 and 58 preferably have a coiled structure, including individual coil segments 62. Importantly, the leads 59 and 60 are coupled to electrodes 57 and 58, respectively, at their mid-points. A connective interface or junction 63 is made between lead 59 and the coil 62.

As many changes are possible to the embodiments of this invention utilizing the teachings thereof, the descriptions above, and the accompanying drawings should be interpreted in the illustrative and not the limited sense.

That which is claimed is:

1. An implantable medical defibrillator electrode apparatus, comprising:
   a. at least one conductive defibrillating electrode said at least one electrode comprising a coiled metallic band and having a cylindrical configuration and a predetermined linear dimension along a first cylindrical axis thereof;
   b. an elongated, flexible conductive lead having first and second ends, said lead first end being connected to said at least one electrode centrally along said first axis; and
   c. means to connect said lead second end to a current source.

2. The implantable medical electrode apparatus of claim 1, wherein said lead first end is connected to said at least one electrode at the mid-point of said cylinder axis.

3. The implantable medical electrode apparatus of claim 1, wherein said lead first end is connected to said at least one electrode at a point within a region consisting of the middle 10 percent of the length of said cylinder axis.

4. The implantable medical electrode apparatus of claim 1, wherein said coiled band has predetermined linear and crossectional dimensions, said coiled band further having a predetermined electrical resistance which is a function of said crossectional dimension.

5. The implantable medical electrode apparatus of claim 1, wherein said electrode is constructed of a predetermined material and has a predetermined crossectional dimension, said electrode further having a predetermined electrical resistance which is a function of said electrode crossectional dimension.

6. The implantable medical electrode apparatus of claim 1, wherein said electrode predetermined linear dimension is at least 4 cm.

7. The implantable medical electrode apparatus of claim 6, wherein said electrode predetermined linear dimension is between 4 and 12 cm.

8. The implantable medical electrode apparatus of claim 1, wherein said electrode is constructed of a conductive material selected from the group of materials consisting of stainless steel, titanium and platinum.

9. The implantable medical electrode apparatus of claim 1, Wherein, said lead conductor is a type of wire selected from the group of wire types consisting of solid wire, a plurality of twisted strands of wire, and a coiled strand of wire.

10. The implantable medical electrode apparatus of claim 1, wherein said lead first end is connected to said electrode mid-point location via a conductive weld joint.

11. The implantable medical electrode apparatus of claim 1, wherein said lead first end is connected to said electrode mid-point location via a mechanical structure.

12. The implantable medical electrode apparatus of claim 1, wherein said means to connect comprises a modular plug end, including a conductive pin.

13. The implantable medical electrode apparatus of claim 1, wherein there are two said electrodes.

14. The implantable medical electrode apparatus of claim 1, wherein said electrode apparatus is a transvenous cardiac defibrillation catheter, the current source being an implantable cardioverter defibrillator.

15. An implantable medical cardiac defibrillation electrode apparatus, comprising:
   a. at least one conductive defibrillation electrode, said at least one electrode comprises a coiled metallic band and having a cylindrical configuration with a predetermined linear dimension along a cylinder axis;
   b. an elongated, flexible conductive lead having first and second ends, said lead first end being connected to said at least one electrode at a mid-point location along said first axis;
   c. means to connect said lead second end to a current source; and
   d. an elongated, flexible cable having a central lumen in which said lead is disposed, said electrode being exteriorly disposed at a predetermined point on said cable.

16. An implantable cardiac defibrillation catheter apparatus, comprising:

a. at least two conductive defibrillation electrodes each having a cylindrical configuration and further comprising a coiled, elongated, continuous metallic band, said electrodes each having a predetermined axial length of between 4 and 12 cm., said metallic band is constructed of a predetermined material and further has predetermined linear and crossectional dimensions such that a predetermined electrical resistance is provided which is a function of said metallic band crossectional dimension and material composition;

b. an elongated, flexible conductive lead connected to each said electrode, each said lead having first and second ends, said lead first end being connected to its respective electrode at a mid-point along said axial length thereof, each said conductive lead further being electrically insulated from the other said lead;

c. means to connect said lead second end to a current source; and d. an elongated flexible cable having a central lumen in which said leads are disposed, said electrodes being exteriorly disposed at predetermined points on said cable, whereby current flows along said leads to said electrodes and a voltage drop occurs between each said electrode mid-point and its respective electrode ends so that extreme fields are minimized.

* * * * *